(12) United States Patent
Grepstad et al.

(10) Patent No.: US 8,666,201 B2
(45) Date of Patent: Mar. 4, 2014

(54) PHOTONIC CRYSTAL SENSOR

(75) Inventors: Jon Olav Grepstad, Oslo (NO); Stig Morten Borch, Oslo (NO); Ib-Rune Johansen, Oslo (NO); Aasmund Sudbo, Oslo (NO); Olav Solgaard, Stanford, CA (US)

(73) Assignees: Sintef, Trondheim (NO); The Board of Trustees of the Leland Stanford Junior University, Palo Alto, CA (US)

( * ) Notice: Subject to any disclaimer, the term of this patent is extended or adjusted under 35 U.S.C. 154(b) by 147 days.

(21) Appl. No.: 13/256,355

(22) PCT Filed: Mar. 24, 2010

(86) PCT No.: PCT/EP2010/053831
§ 371 (c)(1),
(2), (4) Date: Sep. 13, 2011

(87) PCT Pub. No.: WO2010/108952
PCT Pub. Date: Sep. 30, 2010

(65) Prior Publication Data
US 2012/0002913 A1 Jan. 5, 2012

(30) Foreign Application Priority Data
Mar. 24, 2009 (NO) .................................. 20091226

(51) Int. Cl.
*G02B 6/00* (2006.01)
(52) U.S. Cl.
USPC .......................................................... 385/12
(58) Field of Classification Search
None
See application file for complete search history.

(56) References Cited

U.S. PATENT DOCUMENTS

| | | |
|---|---|---|
| 2004/0020423 A1 | 2/2004 | Lewis, III et al. |
| 2004/0264903 A1 | 12/2004 | Dridi et al. |
| 2006/0040376 A1 | 2/2006 | Cunningham et al. |
| 2008/0278722 A1 | 11/2008 | Cunningham et al. |

FOREIGN PATENT DOCUMENTS

| | | |
|---|---|---|
| EP | 1942341 A1 | 7/2008 |
| WO | 2008118211 A2 | 10/2008 |

OTHER PUBLICATIONS

Chan, et al., "Label-free imaging of cancer cells using photonic crystal biosensors and application to cytotoxicity screening of a natural compound library", Sensors and Actuators B, Oct. 26, 2007, vol. 132, No. 2, pp. 418-425; XP022707531.

Lee, et al., "Two-dimensional silicon photonic crystal based biosensing platform for protein detection", Optics Express, Apr. 16, 2007, vol. 15, No. 8, pp. 4530-4535, XP002584294.

Suh, et al., "Mechanically switchable photonic crystal structures based on coupled photonic crystal slabs", Proceedings of the SPIE—The International Society for Optical Engineering, Jul. 9, 2004, vol. 5360, No. 1, pp. 299-306, XP002584555.

International Search Report issued in apn No. PCT/EP2010/053831, mailed Jun. 18, 2010, 4 pages.

(Continued)

*Primary Examiner* — Jerry Rahll
(74) *Attorney, Agent, or Firm* — Rothwell, Figg, Ernst & Manbeck PC

(57) ABSTRACT

This invention relates to an optical sensor element comprising a photonic crystal constituted by a membrane of a chosen transparent material, the membrane being provided with a number of defined openings in a chosen pattern, the pattern being adapted to provide resonance at a chosen wavelength or range of wavelengths, wherein said openings are provided with a reactive material acting as a receptor for a chosen type of molecules, e.g. proteins, the presence of which alters the resonance and/or scattering conditions in the sensor element thus altering the amount of light propagating out of the membrane plane.

26 Claims, 14 Drawing Sheets

(56) References Cited

OTHER PUBLICATIONS

Norwegian Search Report issued in apn No. 20091226, dated Dec. 27, 2010, 2 pages.

Norwegian Search Report issued in apn No. 20091226, dated Oct. 23, 2009, 1 page.

Fan, Shanhui, et al. "Analysis of guided resonances in photonic crystal slabs," Physical Review B, vol. 65, The American Physical Society, 8 pages (Jun. 7, 2002).

Before　　　　　After

| Pattern | Material name | Chem. comp. |
|---|---|---|
|  | Silicon nitride | $Si_3N_4$ |
|  | Silicon | $Si$ |
|  | Silicon oxide | $SiO_2$ |
|  | Gold | $Au$ |

PHOTONIC CRYSTAL SENSOR

CROSS REFERENCE TO RELATED APPLICATION(S)

This application is a 35 U.S.C. §371 National Phase Entry Application from PCT/EP2010/053831, filed Mar. 24, 2010, designating the United States and also claims the benefit of Norwegian Application No. 2009 1226, filed Mar. 24, 2009, the respective disclosures of which are incorporated herein in their entireties by reference.

This invention relates to an optical sensor element comprising a photonic crystal constituted by a membrane of a chosen transparent material, and more specifically the membrane being provided with a number of defined openings (pores) in a chosen pattern, the pattern being adapted to provide resonance at a chosen wavelength or range of wavelengths.

The field of Optical Biosensors has attracted an amazing amount of attention, especially in the last decade, and is based on the measurement of the optical effects of molecules captured on or close to an optical element using reactive materials acting as receivers for specific molecules, often called biorecognition molecules and target molecules, respectively. A large number of articles from numerous group have been published in the recent years. To give updated overviews of the vast amount of articles, a number of reviews are published every year. The work of Xudong Fan, Ian M. White, Siyka I. Shopova, Hongying Zhu, Jonathan D. Suter, Yuze Sun, Analytica Chimica Acta 620 (2008) 8-26, has been extensively referred to and is describing the main technical background for this invention. It focuses on the group of optical biosensors which includes the technical field of this invention, and is based on resent articles published after year 2000.

As is clear from the abovementioned article there are several different types of optical biosensors having different characteristics and advantages, such as differences in sensitivity. A number of solutions are based on measuring the change in refractive index. A problem related to many of the known solutions is that in the refractive index based systems a large quantity of the target material is needed to give a detectable change in the index. Another problem related to the sensitivity is the positioning of the biorecognition molecules. In order to obtain as single molecule sensitivity the target molecules has to be captured in positions where they cause a detectable change in the sensor readout.

One of the solutions discussed in the Xudong article, page 21 and 22 and FIG. 7(A), is a photonic crystal constituted by a membrane of a material transparent to the chosen wavelength and with an optical waveguide coupled to the edges on opposite sides of the crystal. The photonic crystal is constituted by a number of periodic openings and one "defect" constituted by a larger opening in effect providing a Fabry-Perot interferometer with a resonance depending on the characteristics of the "defect". If a target molecule is caught inside the large opening the resonance conditions will change and the presence of the molecule may be detected.

The solution illustrated in FIG. 7(A) of the Xudong article has one major disadvantage. In order to be detected, target molecules need to end up inside this large defect. In order to do this, the test solution has to pass through the defect in some way. This becomes a slow process, when the defect diameter is in the order of 500 nm. Also, the solution is limited to one or very few different target molecules at the time.

In a corresponding waveguide based solution described in an article by M. R. Lee, P. M. Fauchet, Opt. Express, vol. 15, No 8 (2007) 4530 a PC sensor membrane is described which, as in the Xudong article, is coupled to waveguides in the sensor plane so that the light propagate in the PC plane between the waveguides. In order to be used as a single protein sensor it would be necessary to activate only one hole in the sensor to make it possible to detect a single protein being captured in this hole. So far, however, no one has been able to localize the surface activation to a single hole in a PC. But if they managed to localize the surface activation and send the 1 micro liter sample through the small hole in the center using a pressure of 0.1 Bar, calculations shows that the sample will use several months to pass though this very small hole. So the PC above according to the Lee article has the required sensitivity, but has not solved the problem with localized surface activation or analyzing speed. Secondly, all waveguide based sensors have a fundamental problem regarding mechanical alignment, since such a sensor would require positioning in the sub micron range when inserted into the analyzing instrument.

An object of this invention is to provide a solution which allows for localization of the captured molecules including an array containing thousands or millions of optical biosensors each being capable of detecting a few or a single biomacromolecule being captured by the specific biorecognition molecules thus improving the sensitivity of the sensor relative to the known art. Another object of the present invention is to reduce the time needed for detecting the molecules. All objects are obtained using a sensor element and corresponding system as described in the claims.

The present invention is primarily based on the use of plane membrane photonic crystals as described in U.S. Pat. No. 7,412,127 where it is known that photonic crystals can be made to work as mirrors if the characteristics of the crystal are chosen correctly. According to this invention the presence of target molecules in the openings act as defects in the crystal and thus affects the reflection properties of the crystal. Thus the presence of a target molecule may be detected as a change in the reflection or transmission properties of the photonic crystal. Other uses of photonic crystals are shown in WO 2008/118211, where photonic crystals made from biopolymers are discussed, and US2004/264903 where the photonic crystal is used as a waveguide.

A sensor element is obtained having an actuated surface which holds an immobilized specific biorecognition or receptor molecule e.g. an antibody or a single stranded nucleic acid template. These biorecognition molecule will specifically bind (capture) their respective ligand molecules, antigens, or complementary nucleic acid strands. When these molecules hit each other they will form a complex e.g. an antibody-antigen complex or a double stranded nucleic acid molecule.

Specifically the present invention describes a pixel based Photonic Crystal (PC) sensor system where the pixels are the openings (pores) in the membrane where the biorecognition molecules are positioned. Each sensor (pixel) will allow specific detection of a single biomacromolecule i.e protein. At the same time as this very high sensitivity is obtained, a very high dynamical range can be maintained. This type of sensors are especially well suited for incorporation in bioanalytical platforms such as Point of Care in vitro diagnostic (PoC IVD) platforms of the future i.e. instruments that are practical both in size and use and capable of providing results without delay at point of use.

The high sensitivity is obtained by a novel PC sensor where the specific receptor molecules through material specific surface activation are located only on a limited part of the sensor surface, and to the part of the PC surface where the effect of the binding makes a strong change in optical properties. This surface activation will secure that the specific capturing molecules are only situated within the pores that can generate the optical effect while all the involved surfaces that are not part of the interior of these pores are treated to prevent binding of the analyte molecule in question. This can be done by connecting the antibody on i.e. only a $SiO_2$ surface inside the photonic crystal, while the rest of the surface is treated to not adsorb the anti genes or proteins. We obtain this by making a triple stack, e.g. silicon nitride-silicon oxide-silicon nitride.

Other methods for obtaining the specific capturing molecules only within the pores are by removing or deactivating all the capturing molecules that are not positioned inside the pores. This could be obtained by chemical means, radiation or photonic splitting where the treatment is not allowed to reach the interior of the pores. In these systems there it is not essential to have the stacking described above.

There are numerous different types of biomolecules that will specifically bind very strongly to their corresponding counterpart. These includes antibodies binding their corresponding antigens, lectines binding various carbohydrates, single stranded nucleic acid fragments binding their reciprocal nucleic acid fragment and numerous others. Among the mostly used bioreceptor molecules are antibodies or fragments thereof because these biomolecules can easily be developed and produced. In the following antibodies and their reciprocal antigens are used as an example representing all types of biospesific reseptor-ligand systems.

Antibodies (Ab) are protein components of adaptive immune system whose main function are to bind antigens (Ag), or foreign substances in the body, and target them for destruction. Cell clones producing just one specific type of antibodies (monoclonal antibodies) can be isolated and cultivated for producing uniform antibody molecules reacting specifically to a very restricted and defined part of the antigen molecule that originally stimulated the immune system to produce the antibody. The antigens are in natural conditions often parts of virus, bacteria or cancer cells, but may also be blood or tissue component from for example humans that are injected into another species such as mice. The antigens that stimulates the immune system to produce antibodies and that these antibodies bind specifically to are relatively complex molecules (typically proteins) varying in size from a few thousand Daltons to very large complexes (viruses and cells). The antibodies do however only recognize and bind to a very tiny part of these molecules/complexes. An antibody's binding affinity to its respective target antigen is often very high.

Antibodies can be bound to other molecules such as enzymes, fluorophores or to surfaces without any significant change in their binding properties. When the antigen meets the antibody, they will connect.

In the type analytical sensors according to this invention, a specific monoclonal antibody (receptor) is typically coupled by chemical means to a defined area of the surface. When the surface is exposed to a solution containing the reciprocal antigens, the antigens will be captured by the specific antibodies generating an immuno-complex.

The invention will be described below with reference to the accompanying drawings illustrating the invention by way of examples, wherein FIG. 1 illustrates a sensor element according to the invention with one molecule positioned in one opening.

FIGS. 6a-f illustrates different embodiments of the structure of the sensor element according to the invention.

Figure 7A:
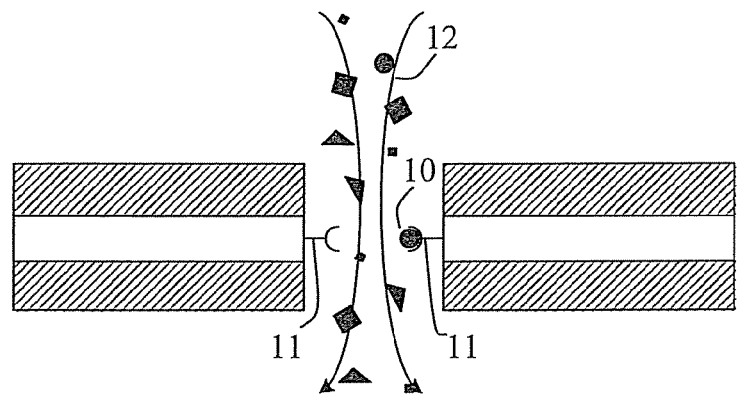

FIG. 7a,b illustrates the process of capturing molecules with two different embodiments of the invention.

Figure 8:
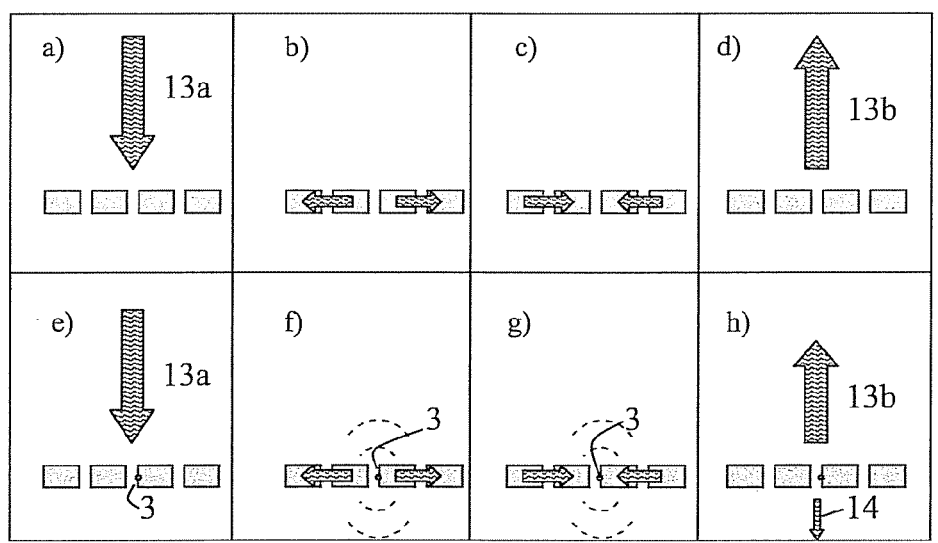
Figure 9:
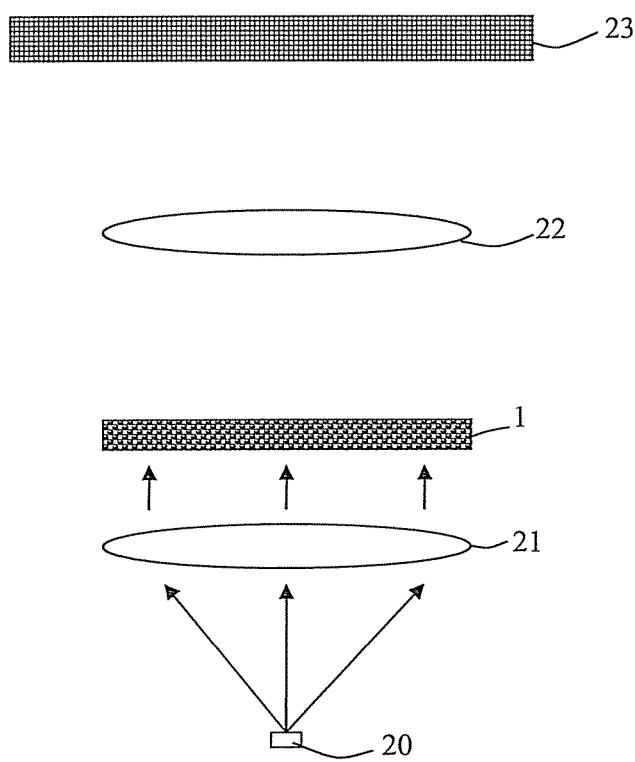

FIG. 8 A simplified illustration of the detection principle. When light at a given wavelength is transmitted towards the PC (a), the light is coupled into the slab (b), reflected (c) and then coupled out (d), and the PC is acting as a mirror. In the case where a biomacromolecule is present (e-h), part of the light starts to transmit as the resonance conditions are changed FIG. 9 illustrates a system according to the invention including a camera for detecting presence of captured molecules.

Figure 10:
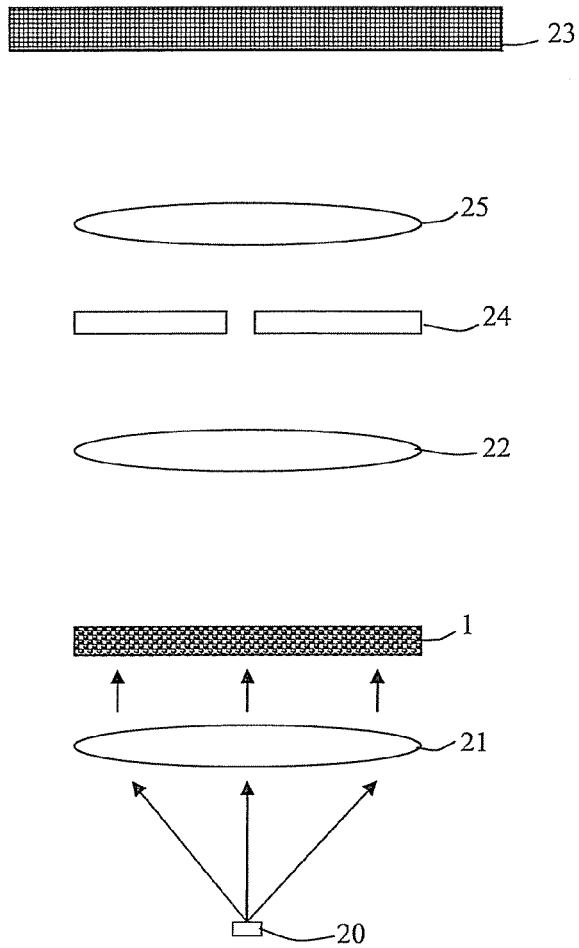
Figure 11:
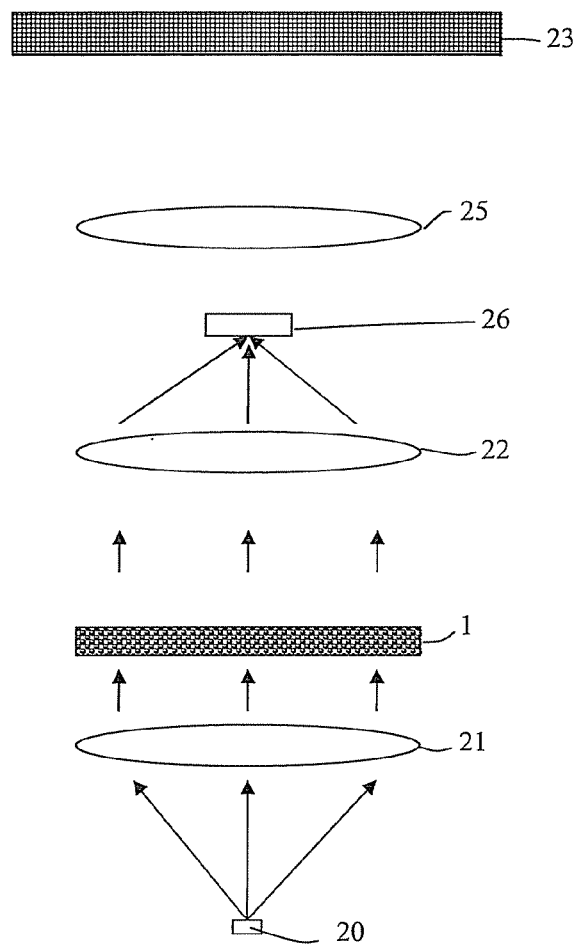

FIG. 10 illustrates an embodiment of the system according to the invention including spatial filter as well as a camera for detecting presence of captured molecules FIG. 11 illustrates an embodiment of the system according to the invention including spatial filter as well as a camera for detecting presence of captured molecules.

Figure 12:
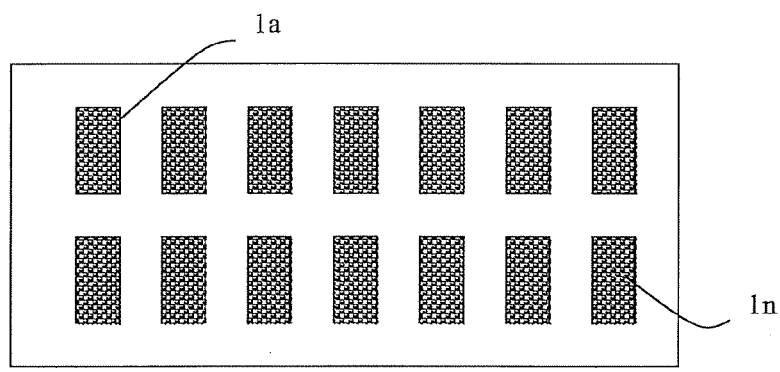

FIG. 12 illustrates a matrix comprising a number of sensor elements according to the invention.

Figure 13:
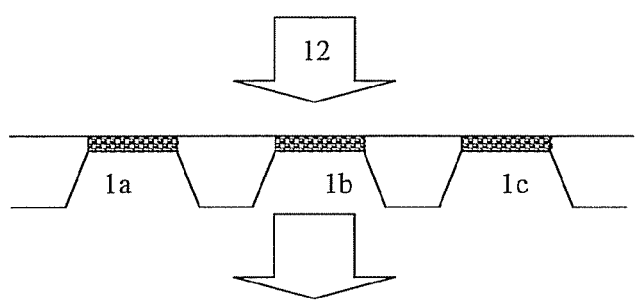

FIG. 13 illustrates the process of capturing target molecules in a matrix as shown in FIG. 12.

Figure 14:
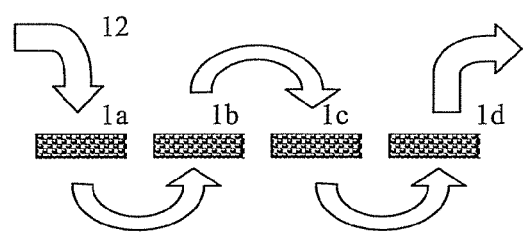
Figure 15A:
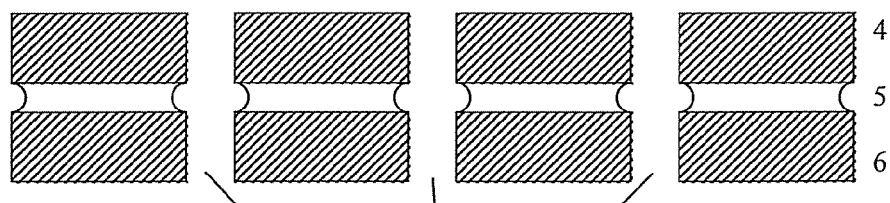
Figure 15B:
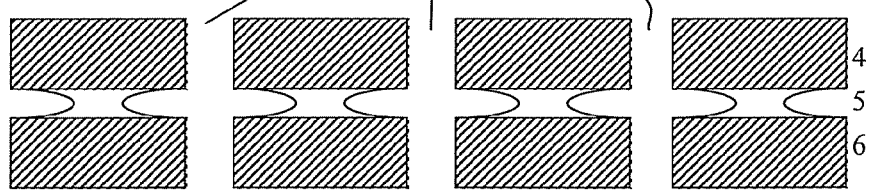
Figure 15C:
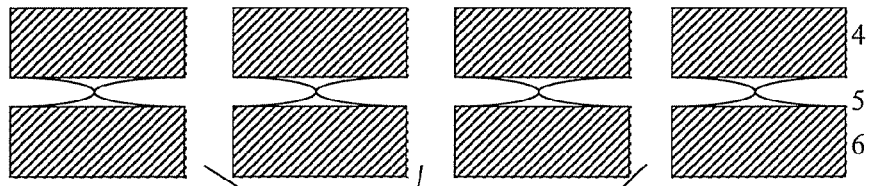
Figure 15D:
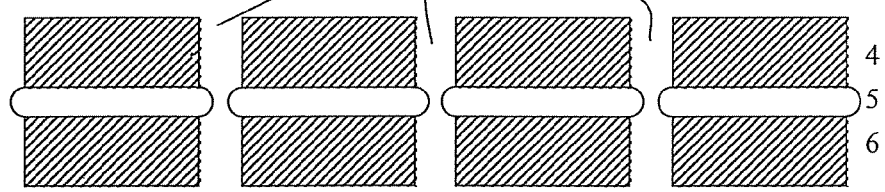

FIG. 14 illustrates an alternative process of capturing target molecules in a matrix as shown in FIG. 12.

FIG. 15a-d illustrates different cross sections of a triplet sensor elements structure where the intermediate layer may have different shapes.

Figure 16:
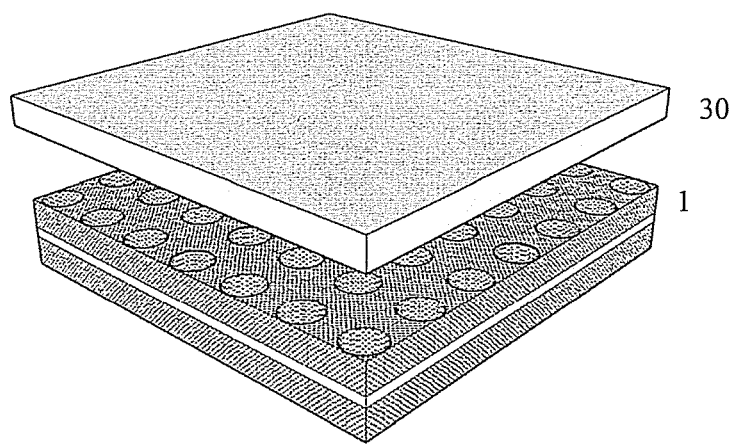

FIG. 16 illustrates an embodiment included as a reflector in a Fabry-Perot.

Figure 17A:
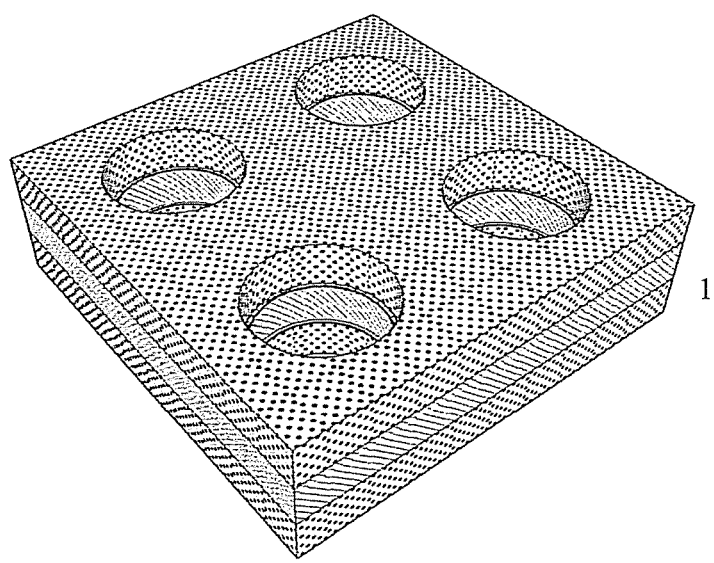
Figure 17B:
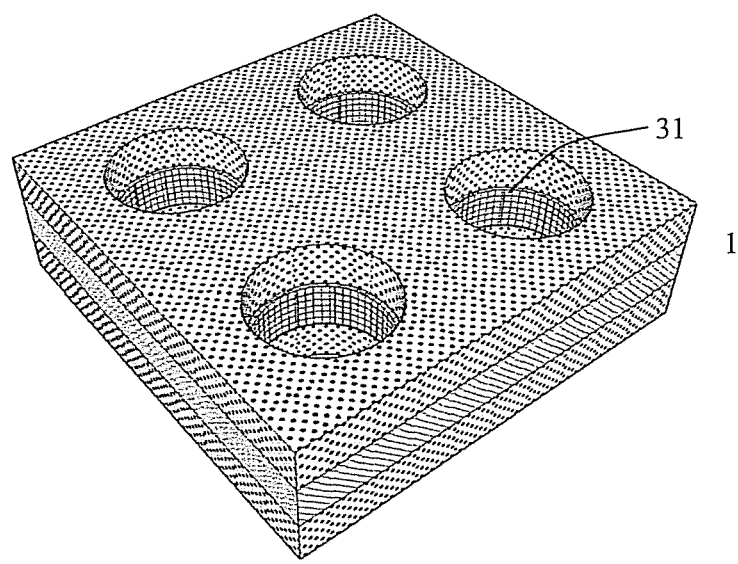
Figure 17C:
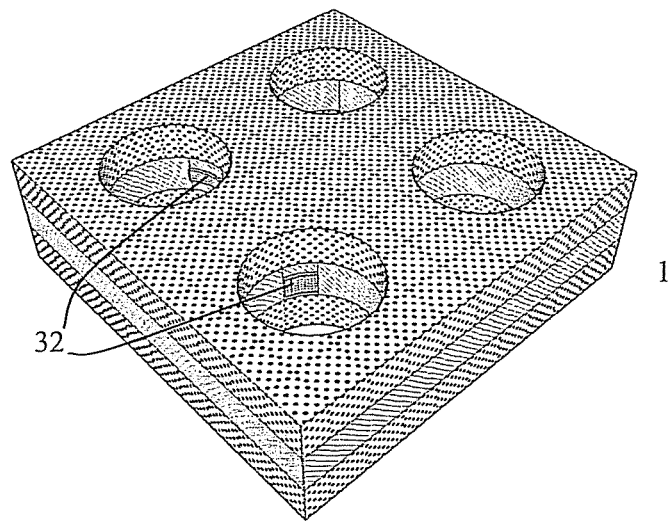

FIG. 17a-c illustrates additional embodiments of the structure of the sensor element.

Figure 1:
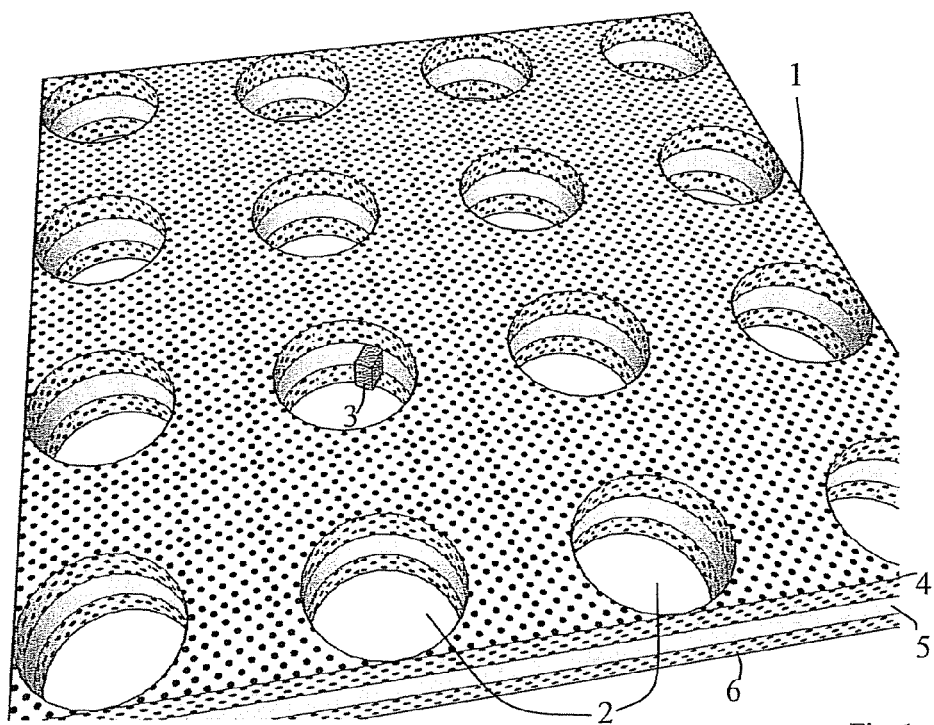

FIG. 1 illustrates part of the sensor element 1 according to the invention. The sensor element has a number of openings 2 constituting the plane photonic crystal, and in one of the openings a target molecule 3 has been captured providing a defect in the photonic crystal structure. The PC element according to the preferred embodiment of the invention is made as a sandwich of three layers 4, 5, 6 wherein the intermediate layer 5 inside the openings is treated with a receptor capable of capturing specific target molecules 3. In the embodiment shown in FIG. 1 the outer layers 4, 6 are made from $Si_3N_4$ and the intermediate layer is $SiO_2$. These materials are fully compatible with silicon processing, and processes for deep reactive ion etching (DRIE) of silicon nitride and silicon oxide are well developed. A silicon nitride membrane is very strong. Silicon nitride also has a large tensile stress, which means that the membrane will be flat and not buckle. The structure with different materials allows us to utilise surface chemistry to selectively connect the capture molecules to one of the layers only. The structure also seems to concentrate the filed around the target molecule.

By reducing the area of the sensor where the binding can occur by limiting it to the intermediate layer in the holes and at the same time optimize the sensitive for this specific region, the sensitivity can be increased 10 to 100 times compared to a sensor where the binding can occur any place at the surface. This is mainly a geometrical effect due to the reduction of binding position to the areas where the sensitivity is high. Binding on top of the surface has limited effect, and should be avoided as it will reduce the chances of binding the target molecules in the preferred positions.

The dimensions of the photonic crystal may depend on many parameters, such as the light wavelength and the optical system into which it should be used. The size of the molecules and possibly virus and bacteria to be detected may also be taken into consideration as some of them will be too large to be lead through the openings.

Figure 2:
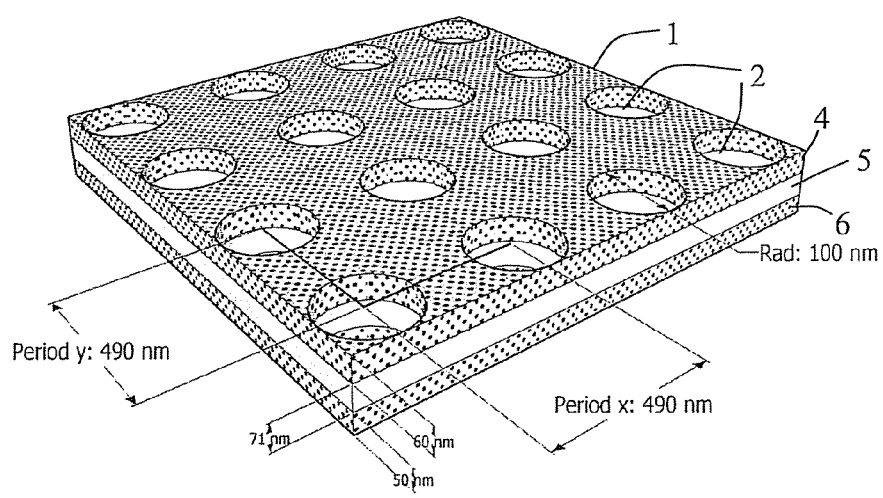
FIG. 2 shows the preferred dimensions of the sensor element.

According to the preferred embodiment the dimensions are as indicated in FIG. 2 where photonic crystal is considered having a period of 490 nm and a hole diameter of 200 nm, a total thickness h of 181 nm, and a 71 nm thick layer in the middle where the receptor molecules are positioned. The area of the inside of the hole is $2\pi r\, h$, while the area of top and bottom within each 490 nm periodic grid is given by $Axy=2(x\, y-\pi r^2)$. By locating the receptor molecules to a position where the sensitivity is high, the sensitivity of the sensor can be increased. In a simplified example, where the sensitivity is zero outside the activated area and 1 on the activated area, the sensitivity could be increased by a factor of around 12 given by the total area divided by the activated area. In practice, this factor is smaller, since the sensitivity distribution is more diffuse. Anyway, in the case where we are looking for a single molecule, it is important that the molecule does not attach on an insensitive part of the surface.

With a sensor element having a membrane size of 2×2 mm the sensor shown in FIG. 2 may have a sensitivity of one single biomacromolecule and a dynamic range of 10.000.000, where the analysis time required is 2-3 minutes because of the large throughput capacity for the fluids to be analyzed. In the shown example the membrane in FIG. 2 being made using materials described in relation to FIG. 1.

Through this the problems regarding sensitivity, localized surface activation, through put and analyzing speed of the sample, and the optical alignment of the sensor by the design described below.

Activation of only the surface position where the maximum influence is obtained by allowing chemical coupling of the receptor (e.g. antibody) on i.e. only a SiO2 surface inside the photonic crystal, while the rest of the surface is treated to not adsorb the antigens or proteins. This is obtained by making a triple stack, with silicon nitride-silicon oxide-silicon nitride. Other stacks may also work, as is illustrated below.

Alternatively it is possible to remove or inactivate any receptor molecules that are coupled to the surfaces that are not part of the holes while protecting the receptor molecules situated within the holes. This could be done both by chemical means and different types of radiation. In this setting the stacking may not be essential.

It is possible to obtain local surface activation by other means as well. By actuating the entire PC structure, and then remove everything except what is inside the holes. This can be done by using fluids with different surface properties, in example a first fluid that sticks to the holes, and thereby protects the insides of the holes during a washing procedure removing everything on the surfaces. The fluid in the holes may then be removed for example by drying, heating, air pressure or other means. Or, the surface activation may be located by using electromagnetic radiation, in example IR, visible, UV, X-ray, alpha, beta and gamma radiation to remove or destroy the specific receptor parts of the surface activation. This may be done on the surface of the crystal, or even inside the crystal at given positions utilizing the properties of the PC.

As another example of local surface activation, it is possible to locate gold inside the holes by using a shadow mask and sputter or evaporate gold onto a tilted wafer. By tilting the wafer, sputtering/evaporating will start to cover the part of the hole that is not shadowed. The mask used for the reactive ion etching (RIE) used to make the holes can be used as the shadow mask as well. If only a small amount of gold is sputtered/evaporated, the shadow mask can be removed by using standard procedures.

To obtain a connection between the antibody inside the Photonic Crystal and the antigen in e.g. a blood sample, these have to meet. This is obtained by sending the sample repeatedly through the holes in the PC, thereby allowing them to meet. Sending the sample repeatedly or back and forth through the sensor is essential in order to increase the probability for the target molecule (antigen) to hit a receptor molecule (antibody).

As the sensor element is constituted by a large number of openings where the target molecules may be capture the sensor is pixel based and each pixel can be used to detect a single biomacromolecule. The sensor consists of many sensor pixels, which allow a very large dynamical range, or in other words detect from 1 to millions of biomacromolecules in a sample. This may be detected using an image sensor, e.g. in a digital camera, providing an image of the optical changes in the sensor element caused by the captured biomacromolecules/target molecules, where the image sensor has a sufficient pixel resolution to detect each single pixel/hole in the sensor element.

Since there are many holes in the sensor, it is possible to send the sample through the sensor fast. This makes rapid analysis possible, compared to a system where there are only a few holes. Calculations show that a 1 micro liter sample will use several months to pass though a hole with 200 nm diameter and 150 nm height using a pressure of 0.1 Bar. If the sensor has $10^6$ holes, the throughput time will be reduced by approximately the same number, allowing the sample to pass through in a few seconds.

In the preferred embodiment of the invention a totally reflecting PC, as described in abovementioned U.S. Pat. No. 7,412,127 is designed for use in transmission. The PC works as a light valve, where the key for opening the valve, are specific receptor-target (e.g. antibody-antigen) reactions in functionalized parts of the crystal. In this way, if no bindings occurring, light will be totally reflected from the grating. When an antigen is bound to the functionalized part of the PC, the PC will no longer be totally reflecting, and the light sensor element (camera) will detect transmitted light. In this configuration we exploit the fact that sensing a small signal change on top of a small signal is easier than sensing the same signal change on top of a large signal.

Figure 3:
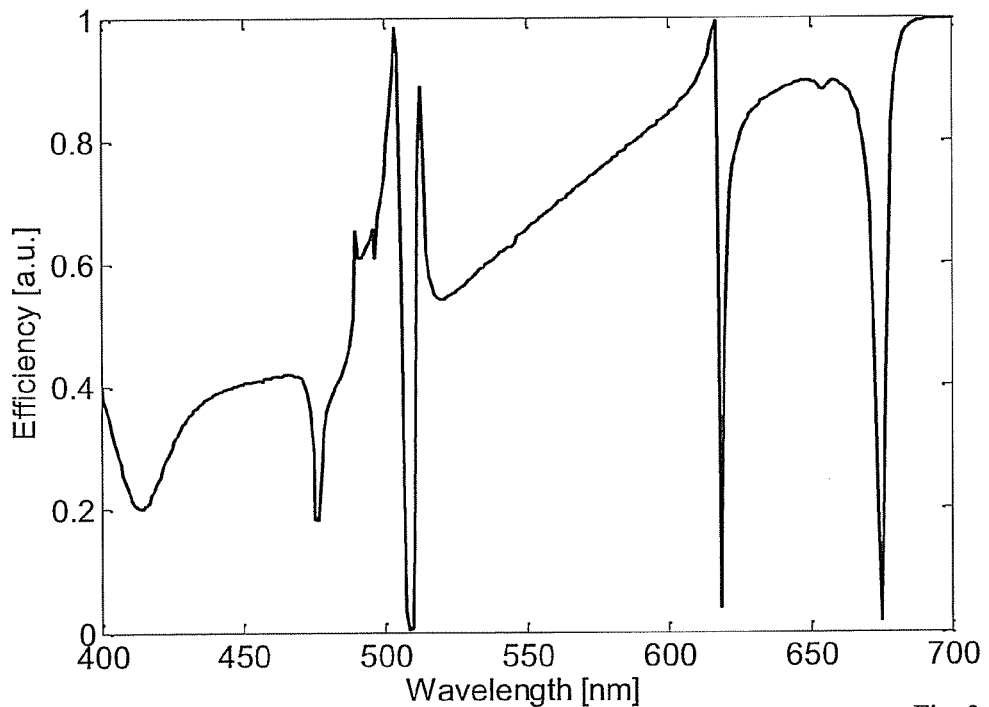
FIG. 3 illustrates the transmission efficiency of a sensor element according to the invention as a function of wavelength.
Figure 4:
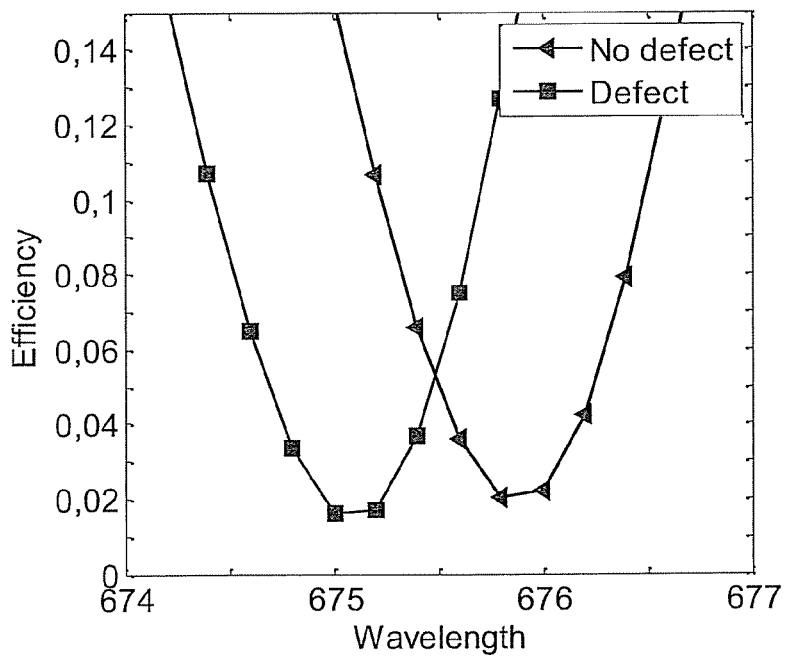
FIG. 4 illustrates the zero order transmission with and without a defect, i.e. captured molecule in the sensor element.

FIG. 3 illustrates the transmission efficiency of the sensor element depending on wavelength while FIG. 4 illustrates the transmission of a PC with and without a defect (macromolecule) placed in a hole.

More in detail the FIG. 4 shows the calculated spectral shift caused by the presence of a biomacromolecule of size 70 nm×20 nm×60 nm. This is a very big molecule, but by examining the figure carefully, we can see that the transmission at 675 nm starts at 2% with no molecule present, and increases to 15%, giving 7.5 times increase in signal. At the start position at 2% signal, the exposure time of the camera and the illumination intensity can be adjusted to give a resolution better than 1000 times, allowing us to measure a molecule with a volume 7500 times smaller than the one in the figure. The detection of a single molecule with diameter below 3 nm should then be possible. The sensitivity of the PC than be further improved by tuning the parameters of the structure.

Figure 5:
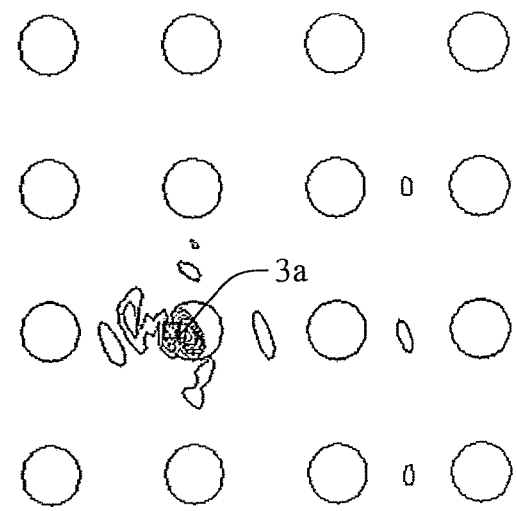
FIG. 5a is the calculated response from a biomacromolecule
FIG. 5b is a view of the difference between the transmission through a sensor element according to the invention with or without captured molecules, as seen with a camera.
Figure 5:
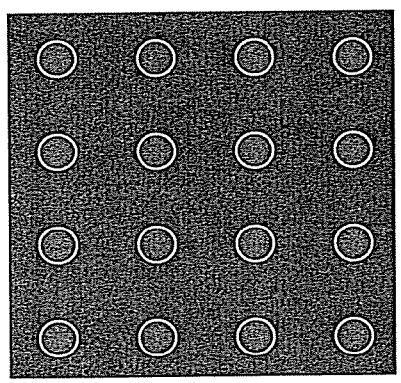
Figure 5:
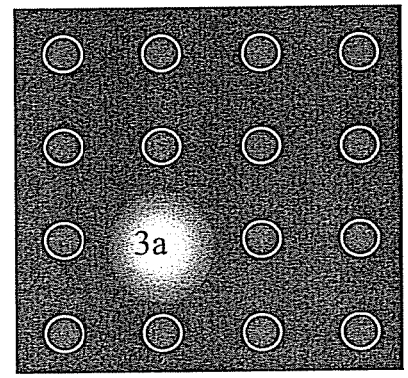

FIG. 5a shows the calculated response caused by the presence of a biomacromolecule 3a. Most of the changes are located to the hole where the biomacromolecule is captured, but some changes appear in the surrounding areas. For some of the resonances and their corresponding wavelengths, the change in transmission may extend a few holes in each direction. FIG. 5b shows over the transmission through the photonic crystal, as measured by a camera before A and after B an antigen-target molecule reaction has taken place. The introduction of a target molecule is changing the optical properties of the PC, and do hence change the transmission for a given wavelength in the surrounding region.

As is clear from FIG. 5b not only the presence of the captured molecule may be detected, but also the position of the molecule, which provides an important advantage for the invention over the known art. Since the changes in transmission properties are localized around the captured biomacromolecule, a camera can be used to count up the number of captured molecules, and thereby extend the dynamical range. Several captured biomacromolecules in each hole will give an increase in signal, and this will also extend the dynamical range.

A PC is a resonator with a Q-factor that depends strongly on the volume of the holes relative to the volume of solid in the PC membrane, and on the angle of incidence of the incident waves driving the resonator. (Ref: S. Fan and J. D. Joannopoulos, "Analysis of guided resonances in photonic crystal slabs," Phys. Rev., vol. B65, p. 235112, 2002) The PC may be designed to ensure that the position of the maximum resonantly enhanced field is very close to where the biomacromolecule is located. A perfectly periodic pattern of holes can give a very high Q-factor (100-5000), and hence a very large resonant enhancement of the field at the biomacromolecule, while ensuring close to 100% reflectance for some wavelengths and close to 100% transmittance for some neighboring wavelengths (Ref: S. Fan and J. D. Joannopoulos).

FIG. 8 explains how the transmission change is localized to the captured molecules. In 8a) a plane wave 13a is transmitted towards the PC. Some of the light is reflected, some exists as a plane wave inside the PC, and some couples into PC modes as shown in b). The light in the PC mode is reflected back by the PC structure, localizing the light to a few periods as illustrated in c). For the chosen wavelength, the PC is designed so that light transmitted through the plane wave and through the localized PC modes interfere destructively such that no transmission is allowed. The light is then reflected back 13b the same way it entered as shown in d). If a biomacromolecule 3 is present as illustrated in e)-h), then there will be localized transmission. The biomacromolecule will influence the refractive index, break the symmetry of the resonator, and scatter light 14 that will be imaged by the camera. The scattered signal amplitude will benefit from the field enhancement inside the PC.

To summarize the invention relates to a photonic crystal sensor where the specific receptor molecules through surface activation are located only on a limited part of the sensor surface, i.e. an opening in the sensor element, and to the part of the PC surface where the effect of the binding makes a strong change in optical properties. The surface for binding may be restricted by using a stack of several materials to locate the binding inside the PC, for example a stack of materials, typically triple, with material 1, material 2, material 3, where 1 and 3 may be the same. The receptor molecules are located to an intermediate material, typically material 2 in the triple stack, and the rest of the sensor surface is treated to prevent unspecific binding of any macromolecule in the sample.

Figure 6:
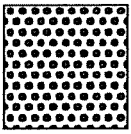
FIG. 6 is an explanation of the patterns used in the drawings
Figure 6:
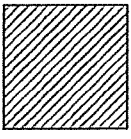
Figure 6:
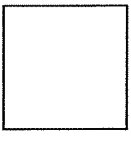
Figure 6:
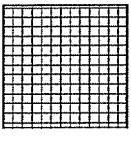
Figure 6A:
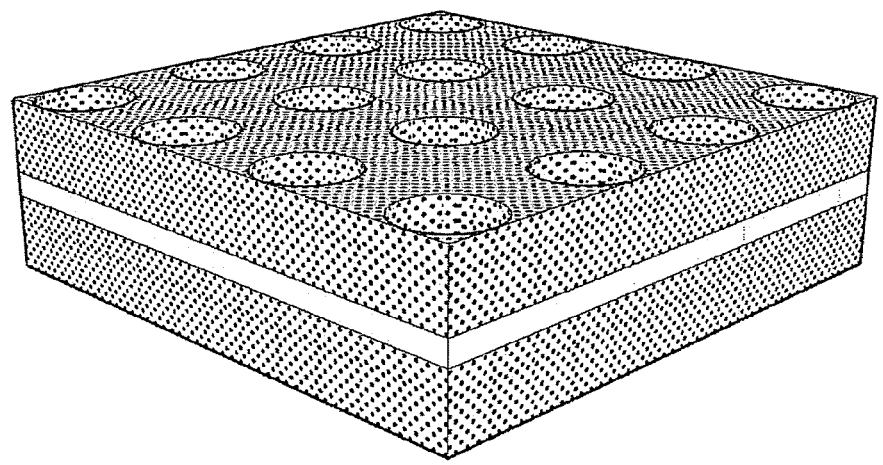
Figure 6B:
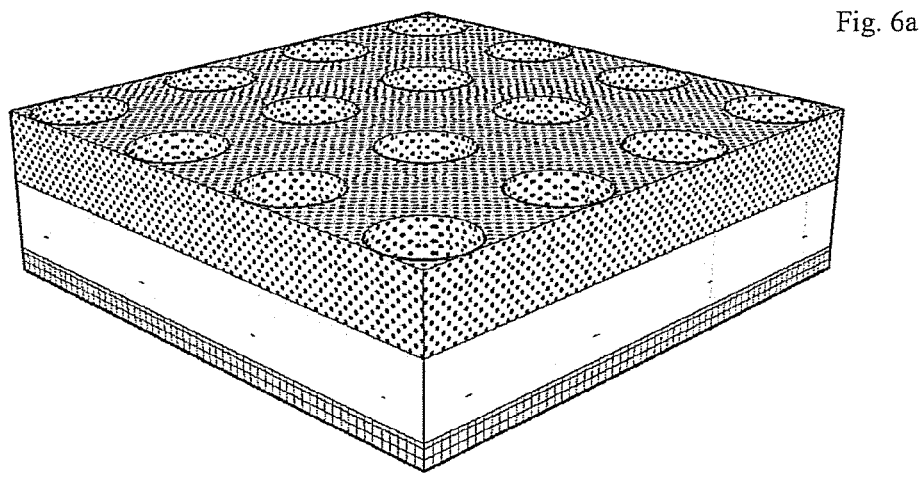
Figure 6C:
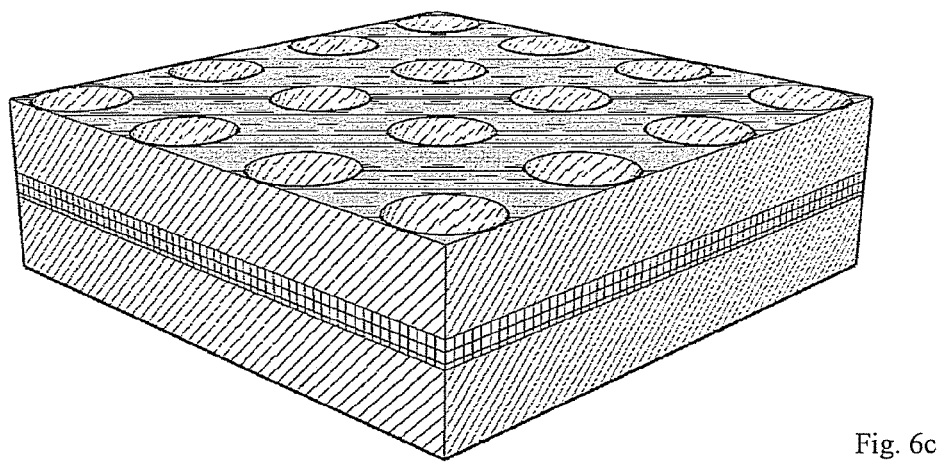
Figure 6D:
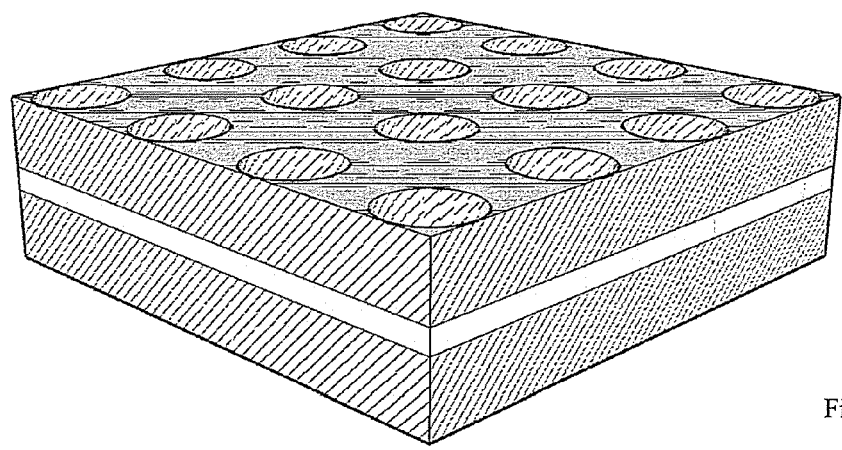
Figure 6E:
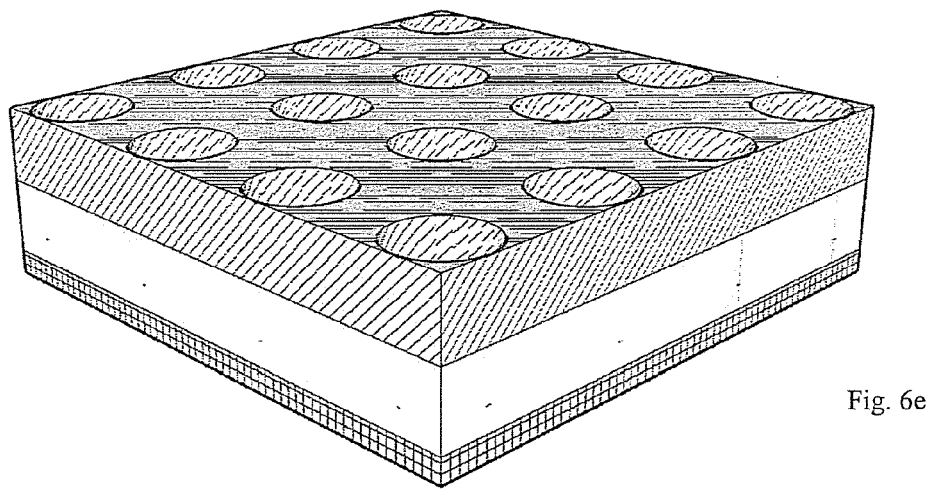
Figure 6F:
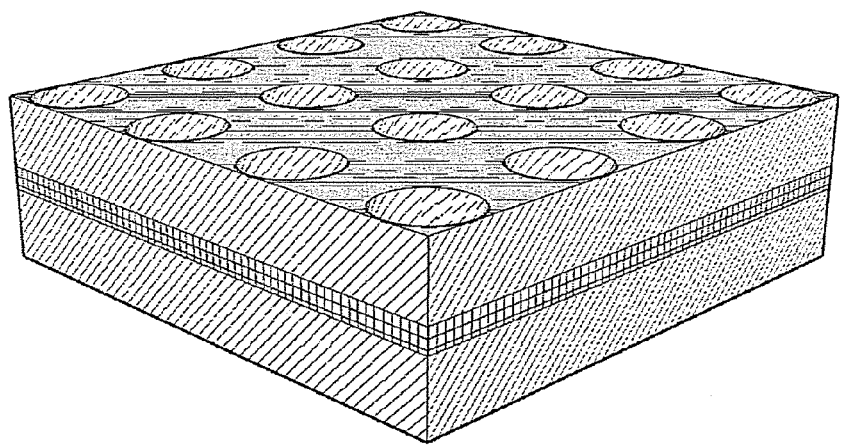

The materials used for producing the sensor element may be different, as illustrated in FIGS. 6, and 6a-6f, where the patterns used for illustrating the different materials is shown in FIG. 6 and the different embodiments are shown in FIGS. 6a-6f. As is discussed above, it is advantageous if the chance for capturing a target molecule is best at the positions giving the largest effect on the optical characteristics, e.g. the transmission efficiency of the photonic crystal. Thus a combination of materials should be used where it is easy to position the biorecognition material inside the holes while it is easy to avoid target molecules being captured outside the holes.

The preferred situation is thus illustrated in FIG. 7a, where a mixture of molecules 12, possibly in a fluid, passes through one hole in the PC and the specified target molecule 10 is captured by the biorecognition molecule 11. The biorecognition molecule may be of any type which may be positioned in the hole, thus among other things having the right size, and capturing the target molecule.

Figure 7B:
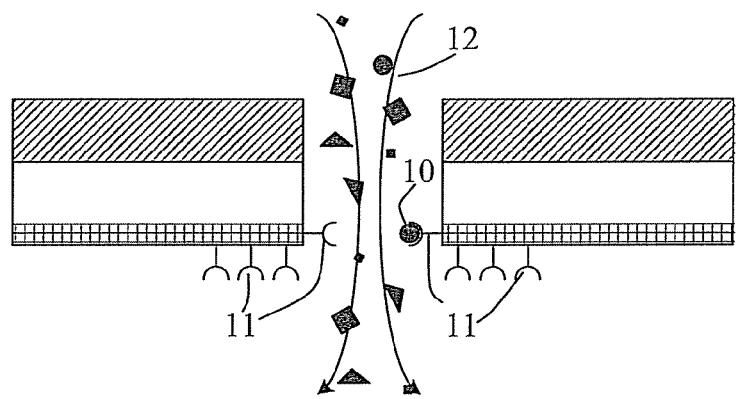

Another possibility is shown in FIG. 7b where the biorecognition molecules 11 are positioned on the lower surface, at the cost of sensitivity. This may, however, be compensated by deactivating or removing the biorecognition molecules at the underside of FIG. 7b by one of the methods discussed above.

As stated above the sensor element may be designed to reflect the light, and start transmitting if a defect in the crystal has occurred. This is a great advantage from a measurement point of view. Starting from a low intensity makes it easier to obtain a good contrast in the measurements. The sensor element according to the invention is primarily aimed at the use in systems where the photonic crystal initially is a reflector where light transmission occurs at the presence of a defect, where the defect is a molecule captured in one of the holes. For detecting the defect a simple setup may be used having a light source on one side of the sensor element and a detector on the other. According to the preferred embodiment of the system according to the invention a camera is used in stead of a simple detector, as shown in FIG. 9.

In FIG. 9 a light source 20, e.g. a tuneable laser or monochromator, emitting light at a suitable range of wavelengths is collimated by a lens 21 and aimed at the photonic crystal membrane 1 constituting the sensor element according to the invention. On the other side of the sensor element 1 an imaging lens 22 projects an image of the sensor element to a camera 23, which is able to record both the presence and position of the defects transmitting the light through the sensor element. FIGS. 10 and 11 shows corresponding systems using different types of spatial filters 24, 25 and necessary lenses 25. FIG. 10 shows how a spatial filter 24 is used to remove scattered light. FIG. 11 shows how an alternative spatial filter 26 is used to remove the zero order light and thereby suppress directly transmitted light from being detected by the camera, and enhance the signal from the scattered or redirected light. This is similar to techniques used in dark field illumination in a transmission microscope. Other types of spatial filtering on the detection side may also be used, i.e. Schlieren optics.

The same kind of techniques can of coarse be used on the illumination side. Any illumination angles not collected by the imaging optics may contribute to increased contrast. An example of this may be the dark field illumination technique used on transmission microscopes. In our invention, collimated light with a well defined angle is preferred.

Given an incoming plane wave, a PC will give a limited number of reflections going in well defined directions. By avoiding these directions in the detection, a reduced background level will be obtained, giving an increased contrast and an increased sensitivity. The detection method can be a dark-field imaging method. The detected field would then not be the transmitted nor reflected plane wave, nor any of the diffracted plane waves, but the scattered spherical waves from the point source that each biomolecule represents.

If polarized light is used, it may be advantageous to perform the detection in the other polarization, as scattering in some cases is known to depolarize light.

Alignment of the sensor in the systems in FIG. 9-11 is not a problem. The sensor is inserted into the instrument and fixed, and since a camera system is used to read out the position of the PC membrane, the exact position is not required. The camera system records the position and transmission of the PC membrane at start, and monitors the change in transmission pixel by pixel.

While it may be possible to position different biorecognition molecules at different positions on the sensor element, and detect the different biomacromolecules as a function of the positions detected by the camera, a matrix of different or similar sensor elements $1a \ldots 1n$ as illustrated in FIG. 12 may also be used in the system. The sensor may be composed of an array of individual PC, and each PC may be actuated with different types of biorecognition or receptor molecules, and thereby allow quantitative detection of several types of macromolecules.

The carrier fluid may then either be lead through the element or elements in one flow through all of the sensor elements as is illustrated in FIG. 13 where the sample 12 will be sent through a series of PCs $1a$, $1b$, $1c$ to make sure that the target molecule and the biorecognition/receptor molecule meets. The PC may be dived in several sections. Between each section, a supporting frame of i.e. silicon may be used to make the sensor more robust. This will be an advantage regarding mechanical properties, since a small PC membrane will withstand higher mechanical forces than a larger membrane.

As illustrated in FIG. 14 the PC may be dived in several sections $1a$, $1b$, $1c$, $1d$, and the sample 12 may be sent through each section in sequence. The sectioning of the membrane allows for individual spotting of biorecognition/receptor molecules. Without a kind of physical sectioning of the sensor, separating the different areas of PC from each other, it will be very difficult to avoid contamination from nearby sections.

This kind of sectioning may be implemented by etching of recesses in silicon and glass wafers, and finally bond these wafers together. This may also be implemented by plastic moulding and bonding.

This kind of sectioning may also be used to implement a particle filter in the first section, to remove particles from blood serum or remove fibrinogen or the other clotting factors from blood plasma.

As shown in FIG. 15$a$-$d$ the holes in the PC may deviate from cylindrical shape depending of the etching technique used where the intermediate layer 5 have different shapes and the intermediate layer 5 holes 2 thus have varying diameters compared to the outer layers 4, 6, and this may be utilized to enhance/optimize the positioning of the biomacromolecule.

Thus the invention is based on the principle of searching for an antigen, typically a protein, actuating the surface so as to hold an antibody, wherein the antibody is specific for a given type of anti genes, viruses or bacteria's.

As an example, by starting with a 5 μL blood sample that is suspected of containing the antigen (disease parameter) of interest. Blood plasma is the liquid component of blood, in which the blood cells are suspended. It makes up about 60% of total blood volume. It is composed of mostly water (90% by volume), and contains dissolved proteins, nutrients, clotting factors, mineral ions, hormones and carbon dioxide (plasma being the main medium for excretory product transportation). Blood plasma is prepared simply by spinning a tube of fresh blood in a centrifuge until the blood cells fall to the bottom of the tube. The blood plasma is then poured or drawn off.

Blood serum is blood plasma without fibrinogen or the other clotting factors, and can be obtained by simply allowing the blood sample too coagulate for 20 to 30 minutes.

The blood plasma or serum will then be used for the analysis.

The largest known proteins are the titins, a component of the muscle sarcomere, with a molecular mass of almost $5 \times 10^{-18}$ gram (3,000 kDa). The typical globular proteins has a diameter of 4 to 8 nm, especially 4-6 nm, and a refractive index of 1.46. As an example we chose a molecule with 7 nm diameter. The volume of this protein is $V=4/3\pi R^3 = 2 \ 10^{-22}$ liter and the weight is $0.2 \ 10^{-18}$ gram.

Below is a comparison of between different sensors based on refractive index and the present invention, based on $2.5 \ 10^{-6}$ liters of sample, and wanting to find a protein with a volume of $2 \ 10^{-22}$ liter.

If we try to measure this with a volume based refractive index sensor, we would need a sensitivity of $dN*Vp/Vs = (1.46-1.33) \times 2 \ 10^{-22}/2.5 \ 10^{-6} = 1.3 \ 10^{-17}$.

If we have a surface binding refractive index sensor with a size of 1×1 mm and with a detection depth of 100 nm, the analyzed volume will be:

$$10^{-3} \text{ m} \times 10^{-3} \text{ m} \times 0.1 \ 10^{-6} \text{ m} = 10^{-13} \text{ m}^3 = 10^{-10} \text{ liter}$$

and the required sensitivity to detect our protein will then be:

$$dN*Vp/Vs = (1.46-1.33) \times 2 \ 10^{-22}/10^{-10} = 2.6 \ 10^{-13}.$$

With an interferometer index sensor, e.g. a typical Mach-Zehnder interferometer with a length of more than 1 mm, and the sensing arm has a width and depth of 1 micrometer the analysed volume will be $10^{-3} \text{ m} \times 10^{-6} \text{ m} \times 10^{-6} \text{ m} = 10^{-15} \text{ m}^3 = 10^{-12}$ liter and the required sensitivity to detect our protein will then be:

$$dN*Vp/Vs = (1.46-1.33) \times 2 \ 10^{-22}/10^{-12} = 2.6 \ 10^{-11}.$$

A typical ring resonator has a radius of 100 μm, giving a length of around 0.6 mm, and the sensing arm has a width and depth of 1 micrometer, and the analysed volume will be $$0.6 \times 10^{-3} \text{ m} \times 10^{-6} \text{ m} \times 10^{-6} \text{ m} = 0.6 \times 10^{-15} \text{ m}^3 = 0.6 \times 10^{-12} \text{ liter}$$

Thus the required sensitivity to detect our protein will then be:

$$dN*Vp/Vs = (1.46 \sim 1.33) \times 2 \ 10^{-22}/(0.6 \times 10^{-12}) = 4.3 \ 10^{-11}.$$

If a single hole in the photonic crystal can be used as a sensor, the detection volume is $$(100 \text{ nm})^3 = 10^{-18} \text{ liter} => dN*Vp/Vs = (1.46 \sim 1.33) \times 2 \ 10^{-22}/10^{-18} = 2.6 \ 10^{-5}.$$

| Single macro molecule detection | | |
|---|---|---|
| | Required refractive index sensitivity | Published refractive index sensitivity[1] |
| Volume index sensor | $1.3 \times 10^{-17}$ | $7 \times 10^{-9}$ |
| Surface Plasmon resonance | $2.6 \times 10^{-13}$ | $10^{-8}$ |
| Interferometric waveguide sensor | $2.6 \times 10^{-11}$ | $10^{-7}$ |

-continued

Single macro molecule detection

| | Required refractive index sensitivity | Published refractive index sensitivity[1] |
|---|---|---|
| Ring resonators, 100 μm radius | $4.3 \times 10^{-11}$ | $10^{-7}$ |
| Photonic crystal sensor | $2.6 \times 10^{-5}$ | $10^{-5}$ |

[1]Ref. Xudong Fan et al.

From the table above, it is obvious that the PC sensor is not suited for refractive index sensing, but ideal for detecting a single protein. This is because the very small volume that can be analyzed.

The invention thus relates to an optical sensor element as well as a system using the sensor element, wherein the sensor element is essentially constituted by a membrane photonic crystal of a chosen transparent material, the membrane being provided with a number of defined openings in a chosen pattern. The pattern being adapted to provide resonance at a chosen wavelength of range of wavelengths, wherein said openings are provided with a reactive material acting as a receptor for a chosen type of molecules, e.g. proteins, the presence of which alters the resonance conditions in the sensor element so that the light propagating out from the plane of the sensor element/membrane changes. This light may be detected by a light sensor, preferably a camera being able to localize the captured molecule.

The sensor is preferably used in transmission setups and thus is made to reflect light that is sent toward the sensor element from a position outside the sensor element plane, the light having a wavelength within the chosen wavelength range when no defect, constituted by a target molecule, is positioned in the openings, and where the presence of such a molecule results in an increase in the light transmitted through the sensor element.

The sensor element is in a porous membrane with multiple defined holes going through, allowing the sample to be transmitted one or several times through the membrane, and thereby increases the probability for binding the target molecule. Other fluids may be transmitted to remove unspecific molecules that are adsorbed.

The sensor element membrane may be divided in sections and supported by solid frames where there is an array of membranes with different specific receptor molecules are mounted.

The readout may be performed using a digital camera, and thereby enables detection of the binding of a single molecule, as a pixel detection, preferably by detecting the transmission of light through the sensor element. The detected image may be treated with chosen methods for enhancing the image, e.g. by removing the background image to remove or calibrate for inaccurate production of the PC sensor element.

The range of wavelengths chosen for the system is related to the characteristics of the sensor element as discussed above in relation to the transmission efficiency. For some purposes several wavelengths may be used for calibration and correction to detect inaccuracies and defects in the PC element other than captured molecules, such as production errors and contaminations. This may be obtained using a superluminescent diode or preferably e tuneable laser as light source.

Preferably both illumination and detection is aligned perpendicular to the sensor element membrane and the illumination being collimated, and the detection may be performed directly or e.g. using spatial filtering to detect scattered light. Deviations from these angles may be contemplated within a large range, the main aspect being that the light propagated at least partially through the membrane plane and/or is reflected from the membrane plane. An embodiment is also possible where the light is applied in the membrane plane but the scattered light from the captured molecules are detected at a point outside the plane, e.g. with a camera being capable of localizing the captured molecules.

The sensor element according to the invention is mainly described as a single membrane with a single pattern, but multilayered structures may be possible having different patterns and with channels capable of letting the carrier fluid pass through the layers. This may provide a three-dimensional photonic crystal. A resonator cavity with 2 or more membranes or crystal layers may be used to concentrate the field close to the captured biomacromolecule to increase the sensitivity.

The diameters of holes, thickness of layers, wavelengths and so on are only given as examples. Different combinations may be advantageous. If all dimensions are reduced by 2, including the wavelength, the total volume of a hole would be reduced by 8, and the sensitivity regarding a biomacromolecule increased by the same factor.

As illustrated in FIG. 16 the photonic crystal (PC) may be combined with a mirror 30 being parallel to the PC and thus providing a Fabry-Perot resonator. This will increase the field inside the structure, thus increasing the intensity of the light scattered by the target molecules 3. Since the PC is a reflecting mirror, the PC can be part of a Fabry Perot structure, and thereby increases the field intensity inside the cavity and inside the PC itself In example, if the PC reflects 99% and the top mirror reflects 99%, the field intensity can be increased for a given wavelength with around 100 times.

This is also an advantage with the triple-stack according to the invention, that the field intensity is increased in the crystal.

In FIG. 17 an embodiment of the invention is illustrated where the triple stack is constituted by a membrane made of silicon nitride bottom layer, silicon in the centre layer and silicon nitride on top. A PC membrane made of Silicon nitride, silicon in the centre layer and silicon nitride on top. This construction has several interesting properties.

1) Silicon has a higher refractive index than silicon oxide, and gives an higher concentration of the optical field in the centre of the hole where the capture molecules are positioned, and gives thereby an increased sensitivity.
2) Silicon is absorbing photons in the visible spectral range, and this is the reason why it can be used in a CCD or CMOS camera. But, in the spectral region around 950 nm to 1100 nm, the absorption in the silicon is so low that it still works good as a material in a PC, and at the same time, the doped silicon used in the CCD sensor can be used as an imaging sensor. This means, that in the spectral region between 950 nm to 1100 nm a high resolution low cost CCD or CMOS silicon camera can be used to read out the SiN PC.
3) By moving the detection up to the spectral range around 1000 nm, the structures (hole diameter and the period) becomes larger, and can be made by standard optical lithography, in example a Stepper.
4) Silicon is a semiconductor, and can be made conductive by doping. This makes it possible to electroplate metals onto silicon. Electroplating and electro less plating may be applied dependent on metal and requirements. In our case we are especially interested in gold.

In FIG. 17b a solution is shown where the silicon, nitride-silicon-silicon nitride stack with a thin layer 31 of gold inside the hole. The gold layer may be applied using electroplating or electro less plating and provides a thin layer of gold that can cover the silicon ring in the center of the PC. These new gold rings have several advantages:
1) It is very easy to connect the capture molecules to a gold surface.
2) If the gold layer is thin enough (less than 2 nm, preferably only a single atom layer), the losses caused by the gold is neglectable.
3) The gold layer itself forms a ring, and it is possible to couple the light to a surface plasmon in the gold ring. It may then be possible to increase the sensitivity of the sensor further, because a silicon-gold interface can support surface plasmon oscillations, and hence allow a higher concentration of the optical fields than silicon without gold. Furthermore, if all the gold rings are identical, they make up an integral part of the PC resonator.
4) The gold may be present on only parts of the ring.

As can be seen in FIG. 17c the gold may also be present in only a part of the ring. This can be obtained by patterning (by i.e. nano imprint) and doping of the silicon in example 40 nm wide lines. These lines are then aligned with the PC holes, making it possible to electroplate gold on only predetermined positions. There are also other methods to obtain only partly covering with gold, including oxidizing the silicon, and selectively remove the oxide by using a mask (or by tilting the structure) and reactive ion etching.

This gold spots 32 inside the PC can be used to position the capture molecules on the optimal position, while permitting surface-plasmon-based optical field enhancement right at the capture molecules.

Other materials than gold may also be used. Gold is only used as an example, since this is a material used in many biosensors.

Also, the high field strength in the sensor element will provide an additional effect in capturing and holding the particles. So-called optical tweezers are capable of manipulating nanometer and micrometer-sized dielectric particles by exerting extremely small forces via a highly focused laser beam. The beam is typically focused by sending it through a microscope objective and the narrowest point of the focused beam, known as the beam waist, contains a very strong electric field gradient. It turns out that dielectric particles are attracted along the gradient to the region of strongest electric field, which is the center of the beam.

For given modes in the photonic crystal according to the invention the intensity close to the walls is very high, due to the cavity resonance. This increasing intensity towards the surface where the biocapture molecules are present will force the target molecules towards this surface, and thereby contribute to increased binding probability. Selection of given wavelengths and give illumination angles will increase the field close to the capture position. Further increase of the field intensity can be obtained by making the PC part of a PF resonator, as mentioned above. In the case of a PC sensor where a given wavelength is used to increase the capture likelihood from a fluid sample that is pushed trough the PC, another wavelength will be optimal for measuring the presence of a captured biomolecule in a dry sensor.

Thus an embodiment of the invention may also be comprised by a sensor with a layer structure of $Si_xN_y$, Si, $Si_xN_y$, and may be provided with a gold ring or spot inside the openings in the photonic crystal. These gold rings or spots may be applied using a electroplating or perform electro less plating, depending on the use and available systems. The biocapture molecules is then connected to the gold.

The surface plasmon resonator caused by the gold ring (or another material) may be connected to the resonator caused by the PC, and thereby increase the sensitivity. The increased field towards the walls to increase capture likelihood may then be utilized, and wavelengths and illumination angles be selected so as to obtain as high fields as possible In order to increase the likelihood of capturing a molecule illumination may be used when the liquid sample is pushed trough the photonic crystal, and an extra mirror may be employed to increase the field further by making a Fabry Perot where the photonic crystal constitutes one of the reflectors.

The invention claimed is:

1. Optical sensor element comprising:
a photonic crystal including a membrane of a transparent material, the membrane being provided with a number of defined openings in a defined pattern, the pattern being adapted to provide resonance for light at a specified wavelength or range of wavelengths,
wherein said openings are provided with a reactive material acting as a receptor for a predetermined type of molecules, and wherein said pattern is adapted to, at the presence of at least two molecules received by a receptor in each of at least two openings, alter the resonance and/or scattering conditions in the sensor element thus altering the amount of light at said specified wavelength or range wavelengths propagating out of the membrane plane from each opening containing one of the at least two molecules,
and wherein said reactive material is only present in said holes.

2. Sensor element according to claim 1, wherein said pattern is configured so that the sensor element acts essentially as a mirror in the specified range of wavelengths, and altering of the resonance conditions caused by the received molecules thus increasing the amount of light transmitted through the sensor element.

3. Sensor element according to claim 1, wherein the membrane is a layered structure constituted by at least two layers of different material, at least one of which being suitable for binding the reactive material.

4. Sensor element according to claim 3, wherein the membrane is constituted by a layered structure including at least three layers thus including two outer layers, the reactive material being positioned at an intermediate layer between said outer layers.

5. Sensor element according to claim 4, wherein the membrane is constituted by a layered structure of $Si_3N_4$, $SiO_2$ and $Si_3N_4$, from top to bottom.

6. Sensor element according to claim 4, wherein the membrane is constituted by a layered structure of $SiO_2$, $Si_3N_4$, and $SiO_2$ from top to bottom.

7. Sensor element according to claim 4, wherein the membrane is constituted by a layered structure of $Si_xN_y$, Si, $Si_xN_y$, from top to bottom.

8. Sensor element according to claim 3, wherein the one layer is treated to bind said receptor and the other layers are treated so as to avoid binding of said molecules.

9. Sensor element according to claim 3, wherein the layers have openings of varying sizes and/or positions so as to provide different optical characteristics at different depth layers.

10. Sensor element according to claim 1, wherein a chosen number of openings are provided with different receptor materials so as to received different types of molecules.

11. A fluidic system configured to force a sample several times through the sensor element according to claim 1 and thereby increase a probability for binding a target molecule.

12. A fluidic system in which several different fluids are transmitted through the sensor element according to claim 1 so as to remove unspecific molecules that are adsorbed.

13. Optical sensor system comprising an optical sensor element, said optical sensor element comprising:
- a photonic crystal including a membrane of a transparent material, the membrane being provided with a number of defined openings in a defined pattern, the pattern being adapted to provide resonance for light at a specified wavelength or range of wavelengths,
- wherein said openings are provided with a reactive material acting as a receptor for a predetermined type of molecules, and wherein said pattern is adapted to, at the presence of at least one molecule received by a receptor in at least one defined opening, alter the resonance and/or scattering conditions in the sensor element thus altering the amount of light at said specified wavelength or range wavelengths propagating out of the membrane plane from an opening containing at least one received molecule,
- and wherein said reactive material is only present in said holes;
- said optical system further comprising:
- a light source directing light at a specified wavelength toward the sensor element and
- a light sensor aimed at the sensor element at an angle relative to the plane of the sensor element sensing the light propagating from the sensor element.

14. Optical sensor system according to claim 13, wherein the light sensor is a digital camera providing a two dimensional image of the sensor element.

15. Optical sensor system according to claim 13, comprising a number of sensor elements being adapted to receive different types of molecules, the system thus being able to simultaneously detect different types of molecules.

16. Optical sensor system according to claim 13, wherein the light source is a tuneable laser.

17. Optical sensor system according to claim 13, wherein the light source is a monochromator.

18. Optical sensor system according to claim 13, wherein the light received from the sensor element is detected using Schlieren optics.

19. Optical sensor system according to claim 13, wherein the light received from the sensor element is detected using spatial filtering.

20. Optical sensor system according to claim 13, wherein the light emitted from said light source and the light received from said sensor element have an optical axis being perpendicular to the sensor element membrane.

21. Optical sensor system according to claim 13, wherein angular filtering of the light source is used to a avoid zero order light to be detected by the light sensor.

22. Optical sensor system according to claim 13, comprising polarizing means for polarizing the light aimed at and/or received from the sensor element.

23. Optical sensor system according to claim 13, where a camera is used to quantify a localized effect caused by a biomacromolecule.

24. Optical sensor system according to claim 13, including a reflective surface positioned in parallel to the sensor element, thus providing a Fabry-Perot resonator between the sensor element and the reflecting surface.

25. Optical sensor system according to claim 13, wherein the optical sensor also comprising means for storing information related to a situation without the presence of said molecules, and comparing the information with signals sensed by said sensor for detecting deviations in the received light and thus the presence of said molecules.

26. Optical sensor system according to claim 13, wherein the sensor element is adapted to reflect light and the light sensor is adapted to sense light being transmitted through the sensor element.

* * * * *